United States Patent
Climent-Johansson et al.

(10) Patent No.: US 7,217,692 B2
(45) Date of Patent: May 15, 2007

(54) COMPLEX OF A HUMAN FOXC2 PROTEIN AND A FOXC2-INTERACTING PROTEIN

(75) Inventors: Isabel Climent-Johansson, Stockholm (SE); Sven Enerbäck, Mölndal (SE)

(73) Assignee: LeanGene AB, Gothenburg (SE)

( * ) Notice: Subject to any disclaimer, the term of this patent is extended or adjusted under 35 U.S.C. 154(b) by 0 days.

(21) Appl. No.: 10/500,941

(22) PCT Filed: Jan. 28, 2003

(86) PCT No.: PCT/SE03/00139

§ 371 (c)(1),
(2), (4) Date: May 5, 2005

(87) PCT Pub. No.: WO03/064467

PCT Pub. Date: Aug. 7, 2003

(65) Prior Publication Data

US 2006/0052293 A1    Mar. 9, 2006

Related U.S. Application Data

(60) Provisional application No. 60/377,349, filed on Apr. 30, 2002.

(30) Foreign Application Priority Data

Jan. 29, 2002    (SE)    ................................. 0200265

(51) Int. Cl.
*A61K 38/00*    (2006.01)

(52) U.S. Cl. ......................................................... 514/12

(58) Field of Classification Search ................... 514/12
See application file for complete search history.

(56) References Cited

OTHER PUBLICATIONS

None.*

* cited by examiner

*Primary Examiner*—Maryam Monshipouri
*Assistant Examiner*—Marsha Tsay
(74) *Attorney, Agent, or Firm*—Fish & Richardson P.C.

(57) ABSTRACT

The present invention relates to complexes of the FOXC2 protein with other proteins, in particular complexes of FOXC2 with proteins designated p621, NOLP, HSC71, FTP3, CLH1, and Kinase A Anchor Protein 84/149 (AKAP). The protein complexes can be used in methods of identifying agents useful for the treatment of medical conditions that can be treated by modulated FOXC2 activity, such as obesity, hypertriglyceridemia, diet-induced insulin resistance, and/or type 2 diabetes.

1 Claim, No Drawings

COMPLEX OF A HUMAN FOXC2 PROTEIN AND A FOXC2-INTERACTING PROTEIN

CROSS REFERENCE TO RELATED APPLICATIONS

This application is a national phase filing under 35 U.S.C. § 371 of international application number PCT/SE03/00139, filed Jan. 28, 2003, which claims the benefit of priority of Swedish application number 0200265-7, filed Jan. 29, 2002, and Provisional application No. 60/377,349, filed Apr. 30, 2002. The disclosures of the prior applications are considered part of (and are incorporated by reference in) the disclosure of this application.

TECHNICAL FIELD

The present invention relates to complexes of the FOXC2 protein with other proteins, in particular complexes of FOXC2 with proteins designated p621, NOLP, HSC71, FTP3, CLH1, and Kinase A Anchor Protein 84/149 (AKAP). The complexes can be used in methods of identifying agents useful for the treatment of medical conditions which can be treated by modulated FOXC2 activity, such as obesity, hypertriglyceridemia, diet-induced insulin resistance, and/or type 2 diabetes.

BACKGROUND ART

Obesity, hyperlipidemia, and insulin resistance are common forerunners of type 2 diabetes mellitus. The human winged helix/forkhead transcription factor gene FOXC2 has been identified as a key regulator of adipocyte metabolism (Cederberg, A. et al. (2001) Cell 106:563–573). Increased FOXC2 expression, in adipocytes, has a pleiotropic effect on gene expression, which leads to a lean and insulin sensitive phenotype. FOXC2 affects adipocyte metabolism by increasing the sensitivity of the beta-adrenergic-cAMP-protein kinase A (PKA) signaling pathway through alteration of adipocyte PKA holoenzyme composition. Increased FOXC2 levels, induced by high fat diet, seem to counteract most of the symptoms associated with obesity, including hypertriglyceridemia and diet-induced insulin resistance; a likely consequence hereof would be protection against type 2 diabetes.

The nucleotide and amino acid sequences of the human FOXC2 protein (SEQ ID NO:1), also known as FKHL14, FREAC-11, or S12, as well as the corresponding mouse mesenchyme forkhead-1 (MFH-1) protein, are known in the art, see Miura, N. et al. (1993) FEBS letters 326: 171–176; Miura, N. et al. (1997) Genomics 41: 489–492; WO 98/54216 and WO 01/60853.

Various mechanisms have been proposed for how FOXC2 function to regulate gene expression. One possibility is that FOXC2 interact with factors that are downstream of the Notch-Delta signaling pathway (Kume, T. et al. (2001) Genes & Development 15:2470–2482). For example, Groucho proteins form transcription repression complexes with bHLH transcriptions factors. It has been shown that Groucho can bind to two FOX proteins, FOXG1 and FOXA2 (Wang, J. -C. et al. (2001) J. Biol. Chem. 275: 18418–18423; Yao, J. et al. (2001) Mol. Cell. Biol. 21:1962–1972), and it was suggested that similar kinds of interactions may occur with FOXC proteins (Kume et al., supra). However, an interaction between the FOXC2 protein and Groucho has not previously been demonstrated. Further, interactions of FOXC2 with any of the proteins designated p621, NOLP, Heat Shock Cognate Protein-71 (HSC71), FTP3, CLH1, or Kinase A Anchor Protein 84/149 (AKAP) have not been previously described.

DISCLOSURE OF THE INVENTION

The present invention is based upon the identification of proteins that interact with FOXC2. The identification of FOXC2-interacting proteins contributes to the understanding of this transcription factor-signaling pathway. Further, such interacting proteins can themselves be useful for the identification of agents useful for the treatment of obesity and diabetes.

Consequently, in a first aspect this invention provides a protein complex of a FOXC2 protein, e.g., a human FOXC2 protein, and a FOXC2-interacting protein, wherein the FOXC2-interacting protein contains an amino acid sequence selected from the group consisting of p621 (e.g., SEQ ID NO:2), NOLP (e.g., SEQ ID NO:3), Heat Shock Cognate Protein-71 (HSC71; e.g., SEQ ID NO:4), FTP3 (e.g., SEQ ID NO:5), CLH1 (e.g., SEQ ID NO:6), and Kinase A Anchor Protein 84/149 (AKAP; e.g., SEQ ID NO:7).

In one embodiment, the invention features a substantially pure protein complex comprising a first polypeptide and a second polypeptide, wherein the first polypeptide comprises the amino acid sequence of SEQ ID NO:1 and the second polypeptide comprises the amino acid sequence of SEQ ID NO:2, 3, 4, 5, 6, or 7.

In some embodiments the first polypeptide comprises a sequence that differs from the amino acid sequence of SEQ ID NO:1 at one or more residues. In addition, in some embodiments the second polypeptide comprises a sequence that differs from the amino acid sequence of SEQ ID NO:2, 3, 4, 5, 6, or 7 at one or more residues. The differences are, preferably, differences or changes at a non-essential residue or a conservative substitution. In one embodiment, the first or second polypeptide includes an amino acid sequence at least about 60% identical to a sequence shown as SEQ ID NO:1, 2, 3, 4, 5, 6, 7, 8, or a fragment thereof. Preferably, the polypeptide is at least 65%, 70%, 75%, 80%, 85%, 90%, 95%, 98%, 99% or more identical to SEQ ID NO:1, 2, 3, 4, 5, 6, or 7. Preferred polypeptide fragments are at least 10%, preferably at least 20%, 30%, 40%, 50%, 60%, 70%, or more, of the length of the sequence shown as SEQ ID NO:1, 2, 3, 4, 5, 6, or 7. The first polypeptide preferably retains the ability to bind to the polypeptide of any of SEQ ID NO:2, 3, 4, 5, 6, or 7. In some examples, the first polypeptide has FOXC2 transcriptional activity. The second polypeptide preferably retains the ability to bind to the polypeptide of SEQ ID NO:1.

The term "substantially pure" as used herein in reference to a given protein complex or polypeptide means that the protein complex or polypeptide is substantially free from other biological macromolecules. For example, the substantially pure protein complex or polypeptide is at least 25%, 50, 75, 80, 85, 95, or 99% pure by dry weight. Purity can be measured by any appropriate standard method known in the art, for example, by column chromatography, polyacrylamide gel electrophoresis, or HPLC analysis.

In another aspect, the invention provides a pharmaceutical composition comprising a therapeutically or prophylactically effective amount of a complex of a human FOXC2 protein and a FOXC2-interacting protein, wherein the FOXC2-interacting protein has an amino acid sequence chosen from the group consisting of SEQ ID NO:2, 3, 4, 5, 6, 7 or 8, and a pharmaceutically acceptable carrier.

Another embodiment of the invention is a pharmaceutical composition for use in the treatment of a medical condition which is treatable by modulated FOXC2 activity, comprising a therapeutically or prophylactically effective amount of a FOXC2-interacting protein having an amino acid sequence chosen from the group consisting of SEQ ID NO:2, 3, 4, 5, 6, 7 or 8, and a pharmaceutically acceptable carrier.

Another embodiment of the invention is a pharmaceutical composition comprising an amount of a protein complex described herein effective for the treatment or prevention of a medical condition associated with FOXC2 expression or activity, and a pharmaceutically acceptable carrier.

Yet another aspect of the invention is a method of modulating FOXC2 expression or activity, the method comprising contacting a cell expressing FOXC2, e.g., human FOXC2, with an amount of a polypeptide, e.g., a substantially pure polypeptide, described herein (e.g., a polypeptide comprising the amino acid sequence of SEQ ID NO:2, 3, 4, 5, 6, or 7), or a nucleic acid encoding the polypeptide, sufficient to modulate the expression or activity of FOXC2 in the cell.

A further aspect of the invention is a method for the treatment or prophylaxis of a medical condition treatable by modulated FOXC2 activity, the method comprising administering to a patient in need of such treatment or prophylaxis an amount of a polypeptide, e.g., a substantially pure polypeptide, described herein (e.g., a polypeptide comprising the amino acid sequence of SEQ ID NO:2, 3, 4, 5, 6, or 7) effective to treat or prevent a medical condition treatable by modulated FOXC2 activity, and a pharmaceutically acceptable carrier.

The medical condition can be a medical condition that is putatively treatable by increased FOXC2 activity, such as obesity, hypertriglyceridemia, diet-induced insulin resistance, or type 2 diabetes. Alternatively, the medical condition can be a medical condition that is putatively treatable by decreased FOXC2 activity, such as anorexia.

The term "treatment" means any treatment of a diseases in a mammal, including: (i) preventing the disease, i.e. causing the clinical symptoms of the disease not to develop (prophylaxis); (ii) inhibiting the disease, i.e. arresting the development of clinical symptoms; and/or (iii) relieving the disease, i.e. causing the regression of clinical symptoms. The term "effective amount" means a dosage sufficient to provide treatment for the disease state being treated. This will vary depending on the patient, the disease and the treatment being effected.

In another aspect, the invention features a method of identifying an agent that modulates (increases or decreases) the formation of a FOXC2 protein complex, the method comprising: (i) contacting a first polypeptide described herein (e.g., a polypeptide comprising the amino acid sequence of SEQ ID NO:1) and a second polypeptide described herein (e.g., a polypeptide comprising the amino acid sequence of SEQ ID NO:2, 3, 4, 5, 6, or 7) in the presence of a candidate agent; (ii) measuring the formation of a complex between the first polypeptide and the second polypeptide in the presence of the candidate agent; and (iii) comparing the formation of the complex between the first polypeptide and the second polypeptide in the presence of the candidate agent with the formation of a complex between the first polypeptide and the second polypeptide in the absence of the candidate agent, to thereby determine whether the candidate agent modulates the formation of a FOXC2 protein complex.

The invention also features a method of identifying an agent that modulates a FOXC2 activity, the method comprising: (i) contacting a first polypeptide described herein (e.g., a polypeptide comprising the amino acid sequence of SEQ ID NO:1) and a second polypeptide described herein (e.g., a polypeptide comprising the amino acid sequence of SEQ ID NO:2, 3, 4, 5, 6, or 7) in the presence of a candidate agent; (ii) measuring a FOXC2 activity of the first polypeptide in the presence of the candidate agent; and (iii) comparing the FOXC2 activity of the first polypeptide in the presence of the candidate agent with the FOXC2 activity of the first polypeptide in the absence of the candidate agent, to thereby determine whether the candidate agent modulates a FOXC2 activity.

The invention also features a method of identifying an agent that modulates a FOXC2 activity, the method comprising: (i) contacting a first polypeptide described herein (e.g., a polypeptide comprising the amino acid sequence of SEQ ID NO:2, 3, 4, 5, 6, or 7) with a candidate agent; (ii) determining that the candidate agent binds to the first polypeptide; (iii) contacting a second polypeptide described herein (e.g., a polypeptide comprising the amino acid sequence of SEQ ID NO:1) with the candidate agent; (iv) measuring a FOXC2 activity of the second polypeptide in the presence of the candidate agent; and (v) comparing the FOXC2 activity of the second polypeptide in the presence of the candidate agent with the FOXC2 activity of the second polypeptide in the absence of the candidate agent, to thereby determine whether the candidate agent modulates a FOXC2 activity.

The first polypeptide and/or the second polypeptide used in the methods can optionally be a substantially pure polypeptide. The methods of the invention can be carried out using a cell-based system or in a cell-free system. An example of a FOXC2 activity that can be measured in the methods of the invention is a FOXC2 transcriptional activity.

The invention also provides a method for the treatment or prophylaxis of a medical condition treatable by modulated FOXC2 activity, the method comprising administering to a patient in need of such treatment or prophylaxis an amount of an agent identified by a method described herein that is effective to treat or prevent a medical condition treatable by modulated FOXC2 activity, and a pharmaceutically acceptable carrier.

The medical condition can be a medical condition that is putatively treatable by increased FOXC2 activity, such as obesity, hypertriglyceridemia, diet-induced insulin resistance, or type 2 diabetes. Alternatively, the medical condition can be a medical condition that is putatively treatable by decreased FOXC2 activity, such as anorexia.

In a further aspect, the invention provides antibodies directed against a complex of a human FOXC2 protein and a FOXC2-interacting protein, which complex is defined above according to the invention. Such antibodies can be prepared according to methods well known in the art. The said antibodies are useful e.g. in methods for the characterization and/or purification of the human FOXC2 protein and/or a FOXC2-interacting protein wherein a specific binding of the antibody to the said complex are utilized. Such methods can include e.g. immunoprecipitation, immunoblotting, or immunoaffinity chromatography. Immunoprecipitation consists on a multiple ordered steps including cells lysis, binding of a specific antigen to an antibody, precipitation of the antigen-antibody complex, washing and dissociation of the antigen from the immune complex (Current Protocols in Molecular Biology, Chapter 10:Analysis of Proteins, 1991, John Wiley & Sons, Inc.) Immunoblotting is a method that combines the resolution of gel electrophoresis with the specificity of immunochemical detection. Immunoblotting can be used to determine a number of important characteristics of protein antigen (i.e., the presence and quantity on a sample, molecular weight, etc.). It can be combined with immunoprecipitation to allow a very sensitive detection of minor antigens and to study specific interactions between antigens (Antibodies, A Laboratory Manual, Chapter 12: Immunoblotting, 1998, Harlow & Lane, CSH). Immunoaffinity chromatography enables for the purification of soluble or membrane-bound protein antigens from cells or homogenized tissues. The technique involves the elution of a single protein from an immunoaffinity column after prior elution of nonspecific absorbed proteins (Current Protocols in Protein Science, Chapter 9: Affinity purification, 1996, John Wiley & Sons, Inc.).

In one embodiment, the invention features a method for purifying a FOXC2-interacting protein, the method comprising: (i) contacting a protein complex comprising a FOXC2 protein comprising the amino acid sequence of SEQ ID NO:1 and a FOXC2-interacting protein comprising the amino acid sequence of SEQ ID NO:2, 3, 4, 5, 6, 7 or 8 with an antibody that binds to the protein complex; and (ii) purifying the FOXC2-interacting protein from the protein complex. An antibody that binds to the protein complex can also be used to purify the protein complex and/or the FOXC2 protein. Any of the first and/or second polypeptides described herein can be used in the antibody-based purification methods of the invention.

Throughout this description the terms "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Below, the invention is described in the appended examples, which are intended to illustrate the invention, without limiting the scope of protection.

EXAMPLES

Example 1

Identification of Putative Positive FOXC2 Interacting Clones by SRS Yeast Two-hybrid System 1.1. Overview of the Sos Recruitment System (SRS)

The Sos Recruitment System (SRS) was used to assay for polypeptides interacting with the human FOXC2 polypeptide. SRS is a modification of the well-known yeast two-hybrid system first described by Fields & Song (1989) Nature 340, 245–246.

In the CytoTrap® SRS (http://www.stratagene.com/vectors/signal_trans/cytotrap; see also Aronheim, A. et al. (1997) Mol. Cell. Biol. 17:3094–3102; and U.S. Pat. No. 5,776,689), proteins are expressed in the cytoplasm where, unlike in the nucleus, they may undergo posttranslational modifications. Protein-protein interactions in the cytoplasm are detected by recruitment of the human Sos gene product (hSos) to the membrane of the cell where it activates the Ras pathway. The CytoTrap system uses the unique yeast strain cdc25H, which contains a temperature-sensitive mutation in the cdc25 gene, the yeast homologue for hSos. This protein, a guanyl nucleotide exchange factor, is essential for activation of the Ras pathway and ultimately for the survival and growth of the cell. The mutation in the cdc25 protein is temperature sensitive; the cells can grow at 25° C. but not at 37° C. This cdc25 mutation can be complemented by the hSos gene product to allow growth at 37°, providing that the hSos protein is localized to the membrane via a protein-protein interaction.

The pMyr vector is designed for cDNA library construction. Gehes are expressed in this vector as a fusion protein with the src myristylation signal that targets and anchors the protein to the cell membrane with the gene product extruding into the cytoplasm. Protein expression is controlled by the GAL1 promoter, which is induced in the presence of galactose but repressed in the presence of glucose.

The bait protein (FOXC2) is expressed as a fusion protein with the hSos protein from the pSos vector. When the cDNA library and the bait construct are cotransformed into the cdc25H yeast strain, the only cells capable of growing at 37° C. on galactose medium are those that have been rescued by a protein-protein interaction recruiting hSos to the cell membrane.

1.2. Cloning of Human FOXC2 in pSos

Human full-length FOXC2 (amino acids 1–501) from the pCB6+ plasmid (Cederberg, A. et al. (2001) Cell 106: 1–20) using CSIX-17 (SEQ ID NO:9) and CSIX-18 (SEQ ID NO:10) primers was amplified by PCR according to standard procedures. The amplified fragment was cloned into the pSos vector (Stratagene catalog No. 217433) using BamHI sites included in the primers. The insert orientation was analyzed by restriction digestion, and the FOXC2 sequence was confirmed by nucleotide sequencing according to standard procedures.

1.3. Expression of pSos-FOXC2 in Yeast

The yeast strain cdc25H (Stratagene catalog No. 217437) was transformed with pSos-FOXC2 according to the protocol (Stratagene; CytoTrap Vector Kit; catalog No. 217438) and plated on SD/PDO-Leu plates. Protein extracts were made as described (Moilanen A. et al. (1998) Mol. Cell Biol. 18: 5128–5139) and subsequently analyzed by PAGE and Western blotting using anti-mouse Sos antibodies (BD Transduction Laboratories; catalog No. S15520-050). The western blot analysis showed protein bands migrating with the expected molecular weight corresponding to Sos-FOXC2 (MW 178 kDa) and Sos (MW 127 kDa). Additional bands of lower molecular weight were observed, probably due to protein degradation occurring during extract preparation or in the yeast cells during growth.

1.4 Transformation of Yeast Cells

A human fetal brain cDNA library (Stratagene catalog No. 975204) was used for transformation of yeast cells. The library was amplified by plating approximately 200,000 colonies/plate of LB-Kan (14-cm diameter). Since the library titer was 0.3×10⁹ cfu/ml a total 50 plates inoculated with 0.66 µl of library suspension per plate were used. Cells were incubated overnight at 37° C. and afterwards, colonies of a pinpoint size were harvested with 2×4 ml of LB using a sterile scraping glass. Additional LB-Kan medium was added to a final volume of 1.5 l. The cell suspension was incubated for 2 h at 37° C. Cells were harvested by centrifugation at 6,000×g for 10 min and the plasmid DNA was prepared using Plasmid Maxi Prep columns (Qiagen catalog No. 12162) following the QIAGEN protocol.

Transformation was performed as described by Stratagene (CytoTrap XR Library Construction Kit; Instruction Manual; catalog No. 200444), with the difference that the transformation was sequential, i.e. carried out in two steps. First, yeast was transformed with the pSOS-FOXC2 plasmid. Cdc25H yeast cells carrying the pSos-FOXC2 plasmid were made competent and transformed with 80 µg of cDNA library DNA. After 72 hours of growth at 25° C. in glucose (-Leu-Ura) the plates were replicated into a galactose medium and incubated at 37° C. for a maximum of 11 days. Transformants were screened following Stratagene protocols for the revertants test.

Approximately 8×10⁵ yeast transformants were screened and 4,000 galactose-dependent candidate clones were obtained. After a parallel growth test at non-permissive temperature in glucose and galactose media, 230 of these clones grew only in galactose and were analyzed further. Clones growing in both glucose and galactose media were considered to be revertants and were therefore discarded.

Example 2

Analysis of Putative Positive Interacting Clones 2.1. Sequence Analysis of Putative FOXC2-interacting Clones Total yeast DNA was prepared as described by Stratagene (CytoTrap XR Library Construction Kit; Instruction Manual; catalog No. 200444). The final pellet was dissolved in 20 µl H$_2$O and used as template for PCR amplification or transformation of *E. coli* cells. 40 µl TOP107' electrocompetent cells were transformed (2.5 kV, 25 µF and 200 Ω) with 2 µl of this DNA. Immediately, 1 ml of SOC medium was added and cells were incubated for 1 hour at 37° C. All cells were plated onto LB-plates containing 30 µg/ml of chloramphenicol. Transformants were used for plasmid DNA preparations (QIAGEN).

In order to amplify prey inserts the extracted yeast DNA was used as template. The PCR reaction was set up by mixing 1 µl of desired yeast DNA, 1×PCR buffer, 5 units TaqPol, 40 pmol each of the primers NA15 (SEQ ID NO:11) and NA1149 (SEQ ID NO:12) and 200 µM dNTP's to a final volume of 50 µl. The following PCR reaction was started: 95° C. for 5 minutes followed by 35 cycles consisting of 30 seconds at 95° C., 30 seconds at 55° C. and 1.5 minute at 72° C. and a final 7 minutes at 72° C. The fragments obtained were purified and sequenced.

Sequence analysis was performed at the level of PCR or plasmid DNA by BLAST homology search against a non-redundant nucleotide database without ESTs (EMBL and GenBank).

2.2. Identification of Seven FOXC2-interacting Proteins

Among the expected false positives, several clones encoding hSos, Ras, and other members of Ras-GTPase family were identified, confirming the ras-signaling pathway readout for this assay. The remaining clones corresponded to previously characterized genes (139 clones) and unknown genes (16 clones). In both cases, some of them were found several times as identical clones, probably due to library amplification. The unknown clones were analyzed further using the validation test in yeast described above. These clones were shown not to express proteins capable of specific interactions with FOXC2, and were therefore disregarded. The clones corresponding to known genes could be classified into the following protein categories: transcription regulators, matrix proteins, transcription factors, kinase-subunits, and nuclear proteins. In total, 43 clones were identified as putative "hits" and further analyzed.

In order to eliminate hits with a nonspecific interaction to FOXC2 (e.g. proteins interacting with the Sos tag-protein) the 43 identified clones were subjected to a false positive test. This was done by co-transformation of cdc25H yeast with each of the hit proteins (pMyrHit) together with (a) pSos-FOXC2; (b) pSos; or (c) as a control, Sos fused to MafB (Stratagene; CytoTrap Vector Kit; catalog No. 217438). Cells that grew in galactose at 37° C. only when transformed with plasmid (a) were considered to represent a true positive interaction. By this procedure, seven proteins (Table I) were identified as putative FOXC2-interacting proteins. For these seven proteins, the above experiment was repeated also with ColI (Stratagene; CytoTrap Vector Kit; catalog No. 217438) as a control, which gave the same results.

To characterize further the interactions between FOXC2 and FOXC2-interacting proteins in yeast, the interaction of Sos-FOXC2 hybrid protein was compared with the one between MafB proteins. MafB proteins are known to form dimers (Kataoka, K. et al. (1994) Mol. Cell. Biol. 14: 7581–7591). The p621 gene exhibited the strongest interaction to FOXC2 followed by FTP3, Groucho and Clathrin. A weaker interaction was observed for PKA anchor protein, NOLP and HSC71.

TABLE I lists putative FOXC2-interacting proteins identified by SRS. Interaction strength is determined relative to the interaction between MafB proteins (++++) during the same conditions.

TABLE I

| Gene | SEQ ID NO: | Accession No. | Interaction strength |
| --- | --- | --- | --- |
| p621 | 2 | AJ242978 (partial mRNA) | ++++ |
| NOLP | 3 | AB017800 | + |
| HSC71 | 4 | BC007276 | + |
| FTP3 | 5 | P55795 | +++ |
| CLH1 | 6 | D21260 | +++ |
| AKAP149 | 7 | X97335 | ++ |
| AES-1/2/ Groucho | 8 | U04241 AAD00654 | +++ |

Example 3

Characterization of FOXC2-interacting Proteins 3.1. p621 p621 (SEQ ID NO:2; partial sequence) is a protein of unknown function that interacts with the Sp1 transcription factor (Gunther, M. et al. (2000) Mol. Cell. Biol. 210: 131–142). The mouse homologue, ATFa-associated factor (mAM), has recently been cloned and characterized (De Grave, F. et al. (2000) 19: 1807–1819). It acts as a transcriptional co-repressor, and contains a bipartite NLS (Nuclear Localization Signal) and an ATPase activity.

In the present SRS screen, the interaction between FOXC2 and the p621 protein in yeast was supported by 12 obtained clones, comprising three different overlapping sequences. On basis of the identified fragments, the p621 region comprising nucleotides 580–1320 is sufficient for the FOXC2-p621 interaction.

3.2. NOLP

NOLP (for "nucleolar-localized protein") is a nucleolar protein cloned from a human fetal brain cDNA library (Ueki, N. et al. (1998) Biochem. Biophys. Res. Comm. 252: 97–102). The NOLP gene encodes a 524-amino acid polypeptide with an *E. coli* helicase-homologous region, an acid-rich domain, three base-rich putative nuclear localization signals, a serine-rich region, and a coiled-coil domain. Northern blot analysis and RT-PCR revealed that NOLP is expressed as a 3.5-kb mRNA in fetal brain, adult brain, and testis. Deletion studies revealed that NOLP contains functional nuclear and nucleolar localization signals. In the present SRS screen, a single NOLP clone was identified, comprising a sequence that starts at the D145 residue of the NOLP sequence (SEQ ID NO:3).

3.3. Heat Shock Cognate Protein-71 (HSC71)

Heat Shock Cognate Protein-71 protein (HSC71; SEQ ID NO:4) has been recently identified from human brain tissues (GenBank Accession No. BC007276). The HSC71 protein contains a hsp70 domain (Pfam-PF00012; Bateman et al. (2002) Nucleic Acids Research 30:276–280) and it is possible to speculate that as other members of this hsp70 superfamily of proteins is involved in protein folding and assembling/disassembling of protein complexes. This has been suggested for the HSC71 protein isolated from rainbow trout (Zafarullah, M. et al. (1992) Eur. J. Biochem. 204: 893–900).

In the present SRS screen, nine HSC71 clones were obtained. They could be categorized into four different overlapping clones (from $K_{67}$ to the stop codon of HSC71 protein).

3.4. FTP3

FTP3 (SEQ ID NO:5) is a Heterogeneous Nuclear Ribonucleoprotein-H' (hnRNP-H'), and is ubiquitously expressed. It comprises three RNA-binding motifs and its function may include pre-mRNA processing and transport. hnRNPs are known to bind heterogeneous nuclear RNA, the transcripts produced by RNA polymerase II (Honoré, B. et al. (1995) J. Biol. Chem.270: 28780–28789). In the present SRS screen, a single FTP3 clone was identified, corresponding to the C-terminal region of FTP3 ($D_{348}$-$A_{449}$).

3.5. CLH1

CLH1 (SEQ ID NO:6) is a human clathrin heavy chain protein. The clathrin heavy chain is the main structural protein of the cytoplasm surface of coated pits and vesicles, involved in receptor-mediated endocytosis, secretion and intracellular transfer of membrane-associated components. It is located at the cytoplasmic phase of coated pits and vesicles and it is readily expressed in most human adult tissues and localized to human chromosome 17 (Dodge, G R. et al. (1991) Genomics 1:174–178).

In the present SRS screen, 13 similar clones were identified, aligning at the N-terminal to $N_{853}$ amino acid residue of the CLH1 sequence.

3.6. AKAP149 (A Kinase Anchor Protein 149)

The effects of individual protein kinases (PKAs) isoforms are determined by their cellular localization, specified through binding to distinct A Kinase Anchor Proteins (AKAPs). AKAP149 (SEQ ID) NO:7; Trendelenburg, G. et al. (1996) Biochem. Biophys. Res. Comm. 225: 313–319) is a putative splicing variant of S-AKAP84 (previously described by Lin et al. (1995) J. Biol. Chem. 270: 27804–27811; GenBank Accession No. U34074) with the important new feature of a RNA-binding motif (KH domain). Trendelenburg et al. showed that AKAP149 was expressed as a 4.2-kb transcript in all epithelial tissues examined, with the strongest signal being detected in prostate and small intestine RNAs. In addition, a 3.2-kb transcript was expressed exclusively in testis. Trendelenburg et al. speculated that AKAP149 is involved in the cAMP-dependent signal transduction pathway and in directing RNA to a specific cellular compartment.

In the present SRS screen, two clones were identified, both containing the entire CDS amino acid sequence of AKAP 149.

3.7. AES1-2/Groucho

AES1-2/Groucho (SEQ ID NO:8) is a human protein exhibiting approximately 50% identity to the N-terminal region of *Drosophila* "enhancer of split Groucho" protein (Miyasaka, H. et al. (1993) Eur. J. Biochem. 216: 343–352). It is possibly involved in the negative regulation of proteins containing WD40 repeats. It has a nuclear localization and is expressed predominantly in muscle, heart and placenta. In the present SRS screen, two clones were identified.

3.8. Summary

In summary, seven FOXC2-interacting proteins were isolated. Two of these proteins (p621 and AES 1-2/groucho) are involved in transcription and could act by repressing FOXC2 transcriptional activity. In addition, three cytoplasmic proteins (AKAP, Clathrin and HSC71) involved in cellular and matrix localization, and protein folding activity, were identified. Finally, two proteins of nuclear localization; one involved in RNA processing (FTP3) and one of unknown function (NOLP), were identified.

Example 4

Expression Profiling of FOXC2-interacting Proteins

To determine the tissue transcript expression profile for the FOXC2-interacting proteins described in Example 3, a computer analysis of Affymetrix chips containing human transcripts from adipose tissue, liver and muscle was performed.

PolyA+ mRNAs were extracted from human tissues from healthy patients using a Dynabeads mRNA Direct™ kit (Dynal A. S., Norway). White adipose, liver and muscle tissues were from biopsies. mRNAs were reverse transcribed using a T7-tagged oligo-dT primer and double-stranded cDNAs were generated. These cDNAs were then amplified and labeled using in vitro transcription (IVT) with T7 RNA polymerase and biotinylated nucleotides. The populations of cRNAs obtained after IVT were purified and fragmented by heat to produce a distribution of RNA fragment sizes from approximately 35 to 200 bases. The Human Genome U95 Set of five GeneChip® probe arrays (Affymetrix; catalog Nos. 900303, 900305, 900307, 900309 and 900311) were hybridized using the recommended buffer overnight at 45° C. with the denatured cRNA samples. The arrays were then washed and stained with R-phycoerythrin streptavidin with the help of an Affyetrix fluidics station. The cartridges were scanned using a Hewlett-Packard confocal scanner and the images were analyzed with the GeneChip 4.1 software (Affymetrix). The identity of the genes represented on the probe arrays was assessed by performing searches using BLAST (Altschul et al. (1990) J. Mol. Biol. 215: 403–410) on available protein sequence databanks.

The results indicated that all identified FOXC2-interacting proteins are present in adipose and liver tissue, except for NOLP and clathrin proteins. In muscle, all identified FOXC2-interacting proteins are present except for NOLP. It can be concluded that the FOXC2-interacting proteins are expressed in tissues involved in energy metabolism and therefore putatively relevant to medical conditions relating to diabetes and obesity.

Example 5

Co-immunoprecipitation

Co-immunoprecipitation of proteins from whole-cell extracts is a valuable approach to test for physical interactions between proteins of interest (Current Protocols in Molecular Biology, Chapter 20: Analysis of protein interactions, 2000, John Wiley & Sons, Inc. 2000). For instance, FOXC2 and each of the identified FOXC2-interacting proteins can be in vitro transcribed/translated under the control of T7 promoter in experiments using a TNT® Coupled Reticulocyte Lysate System (Promega, 2800 Woods Hollow Road, Madison-Wis. 53711, USA) in the presence of $^{35}$S-methionine. The FOXC2-hit complex can be immunoprecipitated using antibodies against FOXC2 or an epitope tag present in one of the proteins expressed as a tag-fusion protein (e.g. c-myc monoclonal or AH-polyclonal antibodies from Clontech). The complex can be resolved by SDS-PAGE. The subsequent exposure of the gel to an X-ray film or phosphorimaging screen can identify the presence of bands of expected size corresponding to the FOXC2-hit complex if these proteins interact to FOXC2.

Example 6

Preparation of Anti-FOXC2 Antibodies

Antibodies are an important tool in the analysis of protein-protein interaction (see e.g. Current Protocols in Molecular Biology, Chapter 11: Immunology, John Wiley & Sons, Inc.). The human FOXC2 protein, or synthetic fragments of the FOXC2 sequence which are specific and antigenic, can be used to immunize animals such as rabbits. Polyclonal antibodies can be raised following standard protocols (Antibodies, A laboratory Manual, Chapter 5: Immunizations, 1988, Harlow & Lane, CHS) and affinity purified from the whole sera when using peptides as antigen. The antibodies will be useful for co-immunoprecipitation of the FOXC2/FOXC2-interacting protein complex, as well as for western blot analysis of the resolved complex.

---

The invention claimed is:

1. A method of identifying an agent that modulates the formation of a FOXC2 protein complex, the method comprising:
   (i) contacting a first polypeptide comprising the amino acid sequence of SEQ ID NO:1 and a second polypeptide comprising the amino acid sequence of SEQ ID NO:2, 3, 4, 5, 6, or 7, in the presence of a candidate agent;
   (ii) measuring the formation of a complex between the first polypeptide and the second polypeptide in the presence of the candidate agent; and
   (iii) comparing the formation of the complex between the first polypeptide and the second polypeptide in the presence of the candidate agent with the formation of a complex between the first polypeptide and the second polypeptide in the absence of the candidate agent, to thereby determine whether the candidate agent modulates the formation of a FOXC2 protein complex.

* * * * *

SEQUENCE LISTING

```
<160> NUMBER OF SEQ ID NOS: 12

<210> SEQ ID NO 1
<211> LENGTH: 501
<212> TYPE: PRT
<213> ORGANISM: Homo sapiens

<400> SEQUENCE: 1

Met Gln Ala Arg Tyr Ser Val Ser Asp Pro Asn Ala Leu Gly Val Val
 1               5                  10                  15

Pro Tyr Leu Ser Glu Gln Asn Tyr Tyr Arg Ala Ala Gly Ser Tyr Gly
            20                  25                  30

Gly Met Ala Ser Pro Met Gly Val Tyr Ser Gly His Pro Glu Gln Tyr
        35                  40                  45

Ser Ala Gly Met Gly Arg Ser Tyr Ala Pro Tyr His His Gln Pro
    50                  55                  60

Ala Ala Pro Lys Asp Leu Val Lys Pro Pro Tyr Ser Tyr Ile Ala Leu
65                  70                  75                  80

Ile Thr Met Ala Ile Gln Asn Ala Pro Glu Lys Lys Ile Thr Leu Asn
                85                  90                  95

Gly Ile Tyr Gln Phe Ile Met Asp Arg Phe Pro Phe Tyr Arg Glu Asn
            100                 105                 110

Lys Gln Gly Trp Gln Asn Ser Ile Arg His Asn Leu Ser Leu Asn Glu
        115                 120                 125

Cys Phe Val Lys Val Pro Arg Asp Asp Lys Lys Pro Gly Lys Gly Ser
    130                 135                 140

Tyr Trp Thr Leu Asp Pro Asp Ser Tyr Asn Met Phe Glu Asn Gly Ser
145                 150                 155                 160

Phe Leu Arg Arg Arg Arg Phe Lys Lys Lys Asp Val Ser Lys Glu
                165                 170                 175

Lys Glu Glu Arg Ala His Leu Lys Glu Pro Pro Ala Ala Ser Lys
            180                 185                 190
```

```
Gly Ala Pro Ala Thr Pro His Leu Ala Asp Ala Pro Lys Glu Ala Glu
            195                 200                 205

Lys Lys Val Val Ile Lys Ser Glu Ala Ala Ser Pro Ala Leu Pro Val
        210                 215                 220

Ile Thr Lys Val Glu Thr Leu Ser Pro Glu Ser Ala Leu Gln Gly Ser
225                 230                 235                 240

Pro Arg Ser Ala Ala Ser Thr Pro Ala Gly Ser Pro Asp Gly Ser Leu
                245                 250                 255

Pro Glu His His Ala Ala Pro Asn Gly Leu Pro Gly Phe Ser Val
            260                 265                 270

Glu Asn Ile Met Thr Leu Arg Thr Ser Pro Pro Gly Gly Glu Leu Ser
            275                 280                 285

Pro Gly Ala Gly Arg Ala Gly Leu Val Val Pro Pro Leu Ala Leu Pro
            290                 295                 300

Tyr Ala Ala Pro Pro Ala Ala Tyr Gly Gln Pro Cys Ala Gln Gly
305                 310                 315                 320

Leu Glu Ala Gly Ala Ala Gly Gly Tyr Gln Cys Ser Met Arg Ala Met
                325                 330                 335

Ser Leu Tyr Thr Gly Ala Glu Arg Pro Ala His Met Cys Val Pro Pro
            340                 345                 350

Ala Leu Asp Glu Ala Leu Ser Asp His Pro Ser Gly Pro Thr Ser Pro
            355                 360                 365

Leu Ser Ala Leu Asn Leu Ala Ala Gly Gln Glu Gly Ala Leu Ala Ala
            370                 375                 380

Thr Gly His His His Gln His Gly His His Pro Gln Ala Pro
385                 390                 395                 400

Pro Pro Pro Pro Ala Pro Gln Pro Gln Pro Thr Pro Gln Pro Gly Ala
                405                 410                 415

Ala Ala Ala Gln Ala Ala Ser Trp Tyr Leu Asn His Ser Gly Asp Leu
            420                 425                 430

Asn His Leu Pro Gly His Thr Phe Ala Ala Gln Gln Thr Phe Pro
            435                 440                 445

Asn Val Arg Glu Met Phe Asn Ser His Arg Leu Gly Ile Glu Asn Ser
450                 455                 460

Thr Leu Gly Glu Ser Gln Val Ser Gly Asn Ala Ser Cys Gln Leu Pro
465                 470                 475                 480

Tyr Arg Ser Thr Pro Pro Leu Tyr Arg His Ala Ala Pro Tyr Ser Tyr
                485                 490                 495

Asp Cys Thr Lys Tyr
            500

<210> SEQ ID NO 2
<211> LENGTH: 514
<212> TYPE: PRT
<213> ORGANISM: Homo sapiens

<400> SEQUENCE: 2

Pro Ser Glu Lys Asn Glu Phe Ser Arg Arg Lys Arg Ser Lys Ser Glu
1               5                   10                  15

Asp Met Asp Asn Val Gln Ser Lys Arg Arg Tyr Met Glu Glu
            20                  25                  30

Tyr Glu Ala Glu Phe Gln Val Lys Ile Thr Ala Lys Gly Asp Ile Asn
            35                  40                  45

Gln Lys Leu Gln Lys Val Ile Gln Trp Leu Leu Glu Glu Lys Leu Cys
```

```
                  50                   55                   60
Ala Leu Gln Cys Ala Val Phe Asp Lys Thr Leu Ala Glu Leu Lys Thr
 65                  70                   75                   80

Arg Val Glu Lys Ile Glu Cys Asn Lys Arg His Lys Thr Val Leu Thr
                     85                   90                   95

Glu Leu Gln Ala Lys Ile Ala Arg Leu Thr Lys Arg Phe Glu Ala Ala
                100                  105                  110

Lys Glu Asp Leu Lys Lys Arg His Glu His Pro Pro Asn Pro Pro Val
                115                  120                  125

Ser Pro Gly Lys Thr Val Asn Asp Val Asn Ser Asn Asn Asn Met Ser
130                  135                  140

Tyr Arg Asn Ala Gly Thr Val Arg Gln Met Leu Glu Ser Lys Arg Asn
145                  150                  155                  160

Val Ser Glu Ser Ala Pro Pro Ser Phe Gln Thr Pro Val Asn Thr Val
                165                  170                  175

Ser Ser Thr Asn Leu Val Thr Pro Pro Ala Val Val Ser Ser Gln Pro
                180                  185                  190

Lys Leu Gln Thr Pro Val Thr Ser Gly Ser Leu Thr Ala Thr Ser Val
                195                  200                  205

Leu Pro Ala Pro Asn Thr Ala Thr Val Val Ala Thr Thr Gln Val Pro
210                  215                  220

Ser Gly Asn Pro Gln Pro Thr Ile Ser Leu Gln Pro Leu Pro Val Ile
225                  230                  235                  240

Leu His Val Pro Val Ala Val Ser Ser Gln Pro Gln Leu Leu Gln Ser
                245                  250                  255

His Pro Gly Thr Leu Val Thr Asn Gln Pro Ser Gly Asn Val Glu Phe
                260                  265                  270

Ile Ser Val Gln Ser Pro Pro Thr Val Ser Gly Leu Thr Lys Asn Pro
                275                  280                  285

Val Ser Leu Pro Ser Leu Pro Asn Pro Thr Lys Pro Asn Asn Val Pro
                290                  295                  300

Ser Val Pro Ser Pro Ser Ile Gln Arg Asn Pro Thr Ala Ser Ala Ala
305                  310                  315                  320

Pro Leu Gly Thr Thr Leu Ala Val Gln Ala Val Pro Thr Ala His Ser
                325                  330                  335

Ile Val Gln Ala Thr Arg Thr Ser Leu Pro Thr Val Gly Pro Ser Gly
                340                  345                  350

Leu Tyr Ser Pro Ser Thr Asn Arg Gly Pro Ile Gln Met Lys Ile Pro
                355                  360                  365

Ile Ser Ala Phe Ser Thr Ser Ser Ala Ala Glu Gln Asn Ser Asn Thr
                370                  375                  380

Thr Pro Arg Ile Glu Asn Gln Thr Asn Lys Thr Ile Asp Ala Ser Val
385                  390                  395                  400

Ser Lys Lys Ala Ala Asp Ser Thr Ser Gln Cys Gly Lys Ala Thr Gly
                405                  410                  415

Ser Asp Ser Ser Gly Val Ile Asp Leu Thr Met Asp Asp Glu Glu Ser
                420                  425                  430

Gly Ala Ser Gln Asp Pro Lys Lys Leu Asn His Thr Pro Val Ser Thr
                435                  440                  445

Met Ser Ser Ser Gln Pro Val Ser Arg Pro Leu Gln Pro Ile Gln Pro
450                  455                  460

Ala Pro Pro Leu Gln Pro Ser Gly Val Pro Thr Ser Gly Pro Ser Gln
465                  470                  475                  480
```

```
Thr Thr Ile His Leu Leu Pro Thr Ala Pro Thr Thr Val Asn Val Thr
            485                 490                 495

His Arg Pro Val Thr Gln Val Thr Thr Arg Leu Pro Val Pro Arg Ala
        500                 505                 510

Pro Ala

<210> SEQ ID NO 3
<211> LENGTH: 524
<212> TYPE: PRT
<213> ORGANISM: Homo sapiens

<400> SEQUENCE: 3

Met His Val Glu Thr Gly Pro Asn Gly Glu Gln Ile Arg Lys His Ala
1               5                   10                  15

Gly Gln Lys Arg Thr Tyr Lys Ala Ile Ser Glu Ser Tyr Ala Phe Leu
            20                  25                  30

Pro Arg Glu Ala Val Thr Arg Phe Leu Met Ser Cys Ser Glu Cys Gln
        35                  40                  45

Lys Arg Met His Leu Asn Pro Asp Gly Thr Asp His Lys Asp Asn Gly
50                  55                  60

Lys Pro Pro Thr Leu Val Thr Ser Met Ile Asp Tyr Asn Met Pro Ile
65                  70                  75                  80

Thr Met Ala Tyr Met Lys His Met Lys Leu Gln Leu Leu Asn Ser Gln
                85                  90                  95

Gln Asp Glu Asp Glu Ser Ser Ile Glu Ser Asp Glu Phe Asp Met Ser
            100                 105                 110

Asp Ser Thr Arg Met Ser Ala Val Asn Ser Asp Leu Ser Ser Asn Leu
        115                 120                 125

Glu Glu Arg Met Gln Ser Pro Gln Asn Leu His Gly Gln Gln Asp Asp
130                 135                 140

Asp Ser Ala Ala Glu Ser Phe Asn Gly Asn Glu Thr Leu Gly His Ser
145                 150                 155                 160

Ser Ile Ala Ser Gly Gly Thr His Ser Arg Glu Met Gly Asp Ser Asn
                165                 170                 175

Ser Asp Gly Lys Thr Gly Leu Glu Gln Asp Glu Gln Pro Leu Asn Leu
            180                 185                 190

Ser Asp Ser Pro Leu Ser Ala Gln Leu Thr Ser Glu Tyr Arg Ile Asp
        195                 200                 205

Asp His Asn Ser Asn Gly Lys Asn Lys Tyr Lys Asn Leu Leu Ile Ser
210                 215                 220

Asp Leu Lys Met Glu Arg Glu Ala Arg Glu Asn Gly Ser Lys Ser Pro
225                 230                 235                 240

Ala His Ser Tyr Ser Ser Tyr Asp Ser Gly Lys Asn Glu Ser Val Asp
                245                 250                 255

Arg Gly Ala Glu Asp Leu Ser Leu Asn Arg Gly Asp Glu Asp Glu Asp
            260                 265                 270

Asp His Glu Asp His Asp Ser Glu Lys Val Asn Glu Thr Asp Gly
        275                 280                 285

Val Glu Ala Glu Arg Leu Lys Ala Phe Asn Met Phe Val Arg Leu Phe
290                 295                 300

Val Asp Glu Asn Leu Asp Arg Met Val Pro Ile Ser Lys Gln Pro Lys
305                 310                 315                 320

Glu Lys Ile Gln Ala Ile Ile Asp Ser Cys Arg Arg Gln Phe Pro Glu
                325                 330                 335
```

-continued

```
Tyr Gln Glu Arg Ala Arg Lys Arg Ile Arg Thr Tyr Leu Lys Ser Cys
            340                 345                 350

Arg Arg Met Lys Arg Ser Gly Phe Glu Met Ser Arg Pro Ile Pro Ser
        355                 360                 365

His Leu Thr Ser Ala Val Ala Glu Ser Ile Leu Ala Ser Ala Cys Glu
    370                 375                 380

Ser Glu Ser Arg Asn Ala Ala Lys Arg Met Arg Leu Glu Arg Gln Gln
385                 390                 395                 400

Asp Glu Ser Ala Pro Ala Asp Lys Gln Cys Lys Pro Glu Ala Thr Gln
                405                 410                 415

Ala Thr Tyr Ser Thr Ser Ala Val Pro Gly Ser Gln Asp Val Leu Tyr
            420                 425                 430

Ile Asn Gly Asn Gly Thr Tyr Ser Tyr His Ser Tyr Arg Gly Leu Gly
        435                 440                 445

Gly Gly Leu Leu Asn Leu Asn Asp Ala Ser Ser Gly Pro Thr Asp
    450                 455                 460

Leu Ser Met Lys Arg Gln Leu Ala Thr Ser Ser Gly Ser Ser Ser Ser
465                 470                 475                 480

Ser Asn Ser Arg Pro Gln Leu Ser Pro Thr Glu Ile Asn Ala Val Arg
                485                 490                 495

Gln Leu Val Ala Gly Tyr Arg Glu Ser Ala Ala Phe Leu Leu Arg Ser
            500                 505                 510

Ala Asp Glu Leu Glu Asn Leu Ile Leu Gln Gln Asn
        515                 520

<210> SEQ ID NO 4
<211> LENGTH: 586
<212> TYPE: PRT
<213> ORGANISM: Homo sapiens

<400> SEQUENCE: 4

Met Asn Pro Thr Asn Thr Val Phe Asp Ala Lys Arg Leu Ile Gly Arg
  1               5                  10                  15

Arg Phe Asp Asp Ala Val Val Gln Ser Asp Met Lys His Trp Pro Phe
             20                  25                  30

Met Val Val Asn Asp Ala Gly Arg Pro Lys Val Gln Val Glu Tyr Lys
         35                  40                  45

Gly Glu Thr Lys Ser Phe Tyr Pro Glu Glu Val Ser Ser Met Val Leu
     50                  55                  60

Thr Lys Met Lys Glu Ile Ala Glu Ala Tyr Leu Gly Lys Thr Val Thr
 65                  70                  75                  80

Asn Ala Val Val Thr Val Pro Ala Tyr Phe Asn Asp Ser Gln Arg Gln
                 85                  90                  95

Ala Thr Lys Asp Ala Gly Thr Ile Ala Gly Leu Asn Val Leu Arg Ile
            100                 105                 110

Ile Asn Glu Pro Thr Ala Ala Ile Ala Tyr Gly Leu Asp Lys Lys
        115                 120                 125

Val Gly Ala Glu Arg Asn Val Leu Ile Phe Asp Leu Gly Gly Gly Thr
    130                 135                 140

Phe Asp Val Ser Ile Leu Thr Ile Glu Asp Gly Ile Phe Glu Val Lys
145                 150                 155                 160

Ser Thr Ala Gly Asp Thr His Leu Gly Gly Glu Asp Phe Asp Asn Arg
                165                 170                 175

Met Val Asn His Phe Ile Ala Glu Phe Lys Arg Lys His Lys Lys Asp
```

```
                    180                 185                 190
Ile Ser Glu Asn Lys Arg Ala Val Arg Arg Leu Arg Thr Ala Cys Glu
            195                 200                 205
Arg Ala Lys Arg Thr Leu Ser Ser Thr Gln Ala Ser Ile Glu Ile
        210                 215                 220
Asp Ser Leu Tyr Glu Gly Ile Asp Phe Tyr Thr Ser Ile Thr Arg Ala
225                 230                 235                 240
Arg Phe Glu Glu Leu Asn Ala Asp Leu Phe Arg Gly Thr Leu Asp Pro
                245                 250                 255
Val Glu Lys Ala Leu Arg Asp Ala Lys Leu Asp Lys Ser Gln Ile His
            260                 265                 270
Asp Ile Val Leu Val Gly Gly Ser Thr Arg Ile Pro Lys Ile Gln Lys
        275                 280                 285
Leu Leu Gln Asp Phe Phe Asn Gly Lys Glu Leu Asn Lys Ser Ile Asn
        290                 295                 300
Pro Asp Glu Ala Val Ala Tyr Gly Ala Ala Val Gln Ala Ala Ile Leu
305                 310                 315                 320
Ser Gly Asp Lys Ser Glu Asn Val Gln Asp Leu Leu Leu Leu Asp Val
                325                 330                 335
Thr Pro Leu Ser Leu Gly Ile Glu Thr Ala Gly Gly Val Met Thr Val
            340                 345                 350
Leu Ile Lys Arg Asn Thr Thr Ile Pro Thr Lys Gln Thr Gln Thr Phe
        355                 360                 365
Thr Thr Tyr Ser Asp Asn Gln Pro Gly Val Leu Ile Gln Val Tyr Glu
        370                 375                 380
Gly Glu Arg Ala Met Thr Lys Asp Asn Asn Leu Leu Gly Lys Phe Glu
385                 390                 395                 400
Leu Thr Gly Ile Pro Pro Ala Pro Arg Gly Val Pro Gln Ile Glu Val
                405                 410                 415
Thr Phe Asp Ile Asp Ala Asn Gly Ile Leu Asn Val Ser Ala Val Asp
            420                 425                 430
Lys Ser Thr Gly Lys Glu Asn Lys Ile Thr Ile Thr Asn Asp Lys Gly
        435                 440                 445
Arg Leu Ser Lys Glu Asp Ile Glu Arg Met Val Gln Glu Ala Glu Lys
        450                 455                 460
Tyr Lys Ala Glu Asp Glu Lys Gln Arg Asp Lys Val Ser Ser Lys Asn
465                 470                 475                 480
Ser Leu Glu Ser Tyr Ala Phe Asn Met Lys Ala Thr Val Glu Asp Glu
                485                 490                 495
Lys Leu Gln Gly Lys Ile Asn Asp Glu Asp Lys Gln Lys Ile Leu Asp
            500                 505                 510
Lys Cys Asn Glu Ile Ile Asn Trp Leu Asp Lys Asn Gln Thr Ala Glu
        515                 520                 525
Lys Glu Glu Phe Glu His Gln Gln Lys Glu Leu Glu Lys Val Cys Asn
        530                 535                 540
Pro Ile Ile Thr Lys Leu Tyr Gln Ser Ala Gly Gly Met Pro Gly Gly
545                 550                 555                 560
Met Pro Gly Gly Phe Pro Gly Gly Ala Pro Ser Gly Gly Ala
                565                 570                 575
Ser Ser Gly Pro Thr Ile Glu Glu Val Asp
            580                 585

<210> SEQ ID NO 5
```

```
<211> LENGTH: 449
<212> TYPE: PRT
<213> ORGANISM: Homo sapiens

<400> SEQUENCE: 5

Met Met Leu Ser Thr Glu Gly Arg Glu Gly Phe Val Val Lys Val Arg
 1               5                  10                  15

Gly Leu Pro Trp Ser Cys Ser Ala Asp Glu Val Met Arg Phe Phe Ser
            20                  25                  30

Asp Cys Lys Ile Gln Asn Gly Thr Ser Gly Ile Arg Phe Ile Tyr Thr
        35                  40                  45

Arg Glu Gly Arg Pro Ser Gly Glu Ala Phe Val Glu Leu Glu Ser Glu
    50                  55                  60

Glu Glu Val Lys Leu Ala Leu Lys Lys Asp Arg Glu Thr Met Gly His
65                  70                  75                  80

Arg Tyr Val Glu Val Phe Lys Ser Asn Ser Val Glu Met Asp Trp Val
                85                  90                  95

Leu Lys His Thr Gly Pro Asn Ser Pro Asp Thr Ala Asn Asp Gly Phe
            100                 105                 110

Val Arg Leu Arg Gly Leu Pro Phe Gly Cys Ser Lys Glu Glu Ile Val
        115                 120                 125

Gln Phe Phe Ser Gly Leu Glu Ile Val Pro Asn Gly Met Thr Leu Pro
    130                 135                 140

Val Asp Phe Gln Gly Arg Ser Thr Gly Glu Ala Phe Val Gln Phe Ala
145                 150                 155                 160

Ser Gln Glu Ile Ala Glu Lys Ala Leu Lys Lys His Lys Glu Arg Ile
                165                 170                 175

Gly His Arg Tyr Ile Glu Ile Phe Lys Ser Ser Arg Ala Glu Val Arg
            180                 185                 190

Thr His Tyr Asp Pro Pro Arg Lys Leu Met Ala Met Gln Arg Pro Gly
        195                 200                 205

Pro Tyr Asp Arg Pro Gly Ala Gly Arg Gly Tyr Asn Ser Ile Gly Arg
    210                 215                 220

Gly Ala Gly Phe Glu Arg Met Arg Arg Gly Ala Tyr Gly Gly Gly Tyr
225                 230                 235                 240

Gly Gly Tyr Asp Asp Tyr Gly Gly Tyr Asn Asp Gly Tyr Gly Phe Gly
                245                 250                 255

Ser Asp Arg Phe Gly Arg Asp Leu Asn Tyr Cys Phe Ser Gly Met Ser
            260                 265                 270

Asp His Arg Tyr Gly Asp Gly Gly Ser Ser Phe Gln Ser Thr Thr Gly
        275                 280                 285

His Cys Val His Met Arg Gly Leu Pro Tyr Arg Ala Thr Glu Asn Asp
    290                 295                 300

Ile Tyr Asn Phe Phe Ser Pro Leu Asn Pro Met Arg Val His Ile Glu
305                 310                 315                 320

Ile Gly Pro Asp Gly Arg Val Thr Gly Glu Ala Asp Val Glu Phe Ala
                325                 330                 335

Thr His Glu Asp Ala Val Ala Ala Met Ala Lys Asp Lys Ala Asn Met
            340                 345                 350

Gln His Arg Tyr Val Glu Leu Phe Leu Asn Ser Thr Ala Gly Thr Ser
        355                 360                 365

Gly Gly Ala Tyr Asp His Ser Tyr Val Glu Leu Phe Leu Asn Ser Thr
    370                 375                 380

Ala Gly Ala Ser Gly Gly Ala Tyr Gly Ser Gln Met Met Gly Gly Met
```

-continued

```
                385                 390                 395                 400
Gly Leu Ser Asn Gln Ser Ser Tyr Gly Gly Pro Ala Ser Gln Gln Leu
                    405                 410                 415
Ser Gly Gly Tyr Gly Gly Tyr Gly Gly Gln Ser Ser Met Ser Gly
            420                 425                 430
Tyr Asp Gln Val Leu Gln Glu Asn Ser Ser Asp Tyr Gln Ser Asn Leu
        435                 440                 445
Ala

<210> SEQ ID NO 6
<211> LENGTH: 1675
<212> TYPE: PRT
<213> ORGANISM: Homo sapiens

<400> SEQUENCE: 6

Met Ala Gln Ile Leu Pro Ile Arg Phe Gln Glu His Leu Gln Leu Gln
  1               5                  10                  15
Asn Leu Gly Ile Asn Pro Ala Asn Ile Gly Phe Ser Thr Leu Thr Met
                 20                  25                  30
Glu Ser Asp Lys Phe Ile Cys Ile Arg Glu Lys Val Gly Glu Gln Ala
             35                  40                  45
Gln Val Val Ile Ile Asp Met Asn Asp Pro Ser Asn Pro Ile Arg Arg
         50                  55                  60
Pro Ile Ser Ala Asp Ser Ala Ile Met Asn Pro Ala Ser Lys Val Ile
 65                  70                  75                  80
Ala Leu Lys Ala Gly Lys Thr Leu Gln Ile Phe Asn Ile Glu Met Lys
                 85                  90                  95
Ser Lys Met Lys Ala His Thr Met Thr Asp Asp Val Thr Phe Trp Lys
            100                 105                 110
Trp Ile Ser Leu Asn Thr Val Ala Leu Val Thr Asp Asn Ala Val Tyr
            115                 120                 125
His Trp Ser Met Glu Gly Glu Ser Gln Pro Val Lys Met Phe Asp Arg
        130                 135                 140
His Ser Ser Leu Ala Gly Cys Gln Ile Ile Asn Tyr Arg Thr Asp Ala
145                 150                 155                 160
Lys Gln Lys Trp Leu Leu Leu Thr Gly Ile Ser Ala Gln Gln Asn Arg
                165                 170                 175
Val Val Gly Ala Met Gln Leu Tyr Ser Val Asp Arg Lys Val Ser Gln
            180                 185                 190
Pro Ile Glu Gly His Ala Ala Ser Phe Ala Gln Phe Lys Met Glu Gly
        195                 200                 205
Asn Ala Glu Glu Ser Thr Leu Phe Cys Phe Ala Val Arg Gly Gln Ala
    210                 215                 220
Gly Gly Lys Leu His Ile Ile Glu Val Gly Thr Pro Pro Thr Gly Asn
225                 230                 235                 240
Gln Pro Phe Pro Lys Lys Ala Val Asp Val Phe Phe Pro Pro Glu Ala
                245                 250                 255
Gln Asn Asp Phe Pro Val Ala Met Gln Ile Ser Glu Lys His Asp Val
            260                 265                 270
Val Phe Leu Ile Thr Lys Tyr Gly Tyr Ile His Leu Tyr Asp Leu Glu
        275                 280                 285
Thr Gly Thr Cys Ile Tyr Met Asn Arg Ile Ser Gly Glu Thr Ile Phe
    290                 295                 300
Val Thr Ala Pro His Glu Ala Thr Ala Gly Ile Ile Gly Val Asn Arg
```

-continued

```
            305                 310                 315                 320
Lys Gly Gln Val Leu Ser Val Cys Val Glu Glu Asn Ile Ile Pro
                325                 330                 335
Tyr Ile Thr Asn Val Leu Gln Asn Pro Asp Leu Ala Leu Arg Met Ala
                340                 345                 350
Val Arg Asn Asn Leu Ala Gly Ala Glu Glu Leu Phe Ala Arg Lys Phe
                355                 360                 365
Asn Ala Leu Phe Ala Gln Gly Asn Tyr Ser Glu Ala Ala Lys Val Ala
                370                 375                 380
Ala Asn Ala Pro Lys Gly Ile Leu Arg Thr Pro Asp Thr Ile Arg Arg
385                 390                 395                 400
Phe Gln Ser Val Pro Ala Gln Pro Gly Gln Thr Ser Pro Leu Leu Gln
                405                 410                 415
Tyr Phe Gly Ile Leu Leu Asp Gln Gly Gln Leu Asn Lys Tyr Glu Ser
                420                 425                 430
Leu Glu Leu Cys Arg Pro Val Leu Gln Gln Gly Arg Lys Gln Leu Leu
                435                 440                 445
Glu Lys Trp Leu Lys Glu Asp Lys Leu Glu Cys Ser Glu Glu Leu Gly
                450                 455                 460
Asp Leu Val Lys Ser Val Asp Pro Thr Leu Ala Leu Ser Val Tyr Leu
465                 470                 475                 480
Arg Ala Asn Val Pro Asn Lys Val Ile Gln Cys Phe Ala Glu Thr Gly
                485                 490                 495
Gln Val Gln Lys Ile Val Leu Tyr Ala Lys Lys Val Gly Tyr Thr Pro
                500                 505                 510
Asp Trp Ile Phe Leu Leu Arg Asn Val Met Arg Ile Ser Pro Asp Gln
                515                 520                 525
Gly Gln Gln Phe Ala Gln Met Leu Val Gln Asp Glu Glu Pro Leu Ala
                530                 535                 540
Asp Ile Thr Gln Ile Val Asp Val Phe Met Glu Tyr Asn Leu Ile Gln
545                 550                 555                 560
Gln Cys Thr Ala Phe Leu Leu Asp Ala Leu Lys Asn Asn Arg Pro Ser
                565                 570                 575
Glu Gly Pro Leu Gln Thr Arg Leu Leu Glu Met Asn Leu Met His Ala
                580                 585                 590
Pro Gln Val Ala Asp Ala Ile Leu Gly Asn Gln Met Phe Thr His Tyr
                595                 600                 605
Asp Arg Ala His Ile Ala Gln Leu Cys Glu Lys Ala Gly Leu Leu Gln
                610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
                645                 650                 655
Ser Leu Ser Val Glu Asp Ser Leu Glu Cys Leu Arg Ala Met Leu Ser
                660                 665                 670
Ala Asn Ile Arg Gln Asn Leu Gln Ile Cys Val Gln Val Ala Ser Lys
                675                 680                 685
Tyr His Glu Gln Leu Ser Thr Gln Ser Leu Ile Glu Leu Phe Glu Ser
                690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
                725                 730                 735
```

-continued

```
Lys Thr Gly Gln Ile Lys Glu Val Glu Arg Ile Cys Arg Glu Ser Asn
            740                 745                 750
Cys Tyr Asp Pro Glu Arg Val Lys Asn Phe Leu Lys Glu Ala Lys Leu
            755                 760                 765
Thr Asp Gln Leu Pro Leu Ile Ile Val Cys Asp Arg Phe Asp Phe Val
            770                 775                 780
His Asp Leu Val Leu Tyr Leu Tyr Arg Asn Asn Leu Gln Lys Tyr Ile
785                 790                 795                 800
Glu Ile Tyr Val Gln Lys Val Asn Pro Ser Arg Leu Pro Val Val Ile
            805                 810                 815
Gly Gly Leu Leu Asp Val Asp Cys Ser Glu Asp Val Ile Lys Asn Leu
            820                 825                 830
Ile Leu Val Val Arg Gly Gln Phe Ser Thr Asp Glu Leu Val Ala Glu
            835                 840                 845
Val Glu Lys Arg Asn Arg Leu Lys Leu Leu Leu Pro Trp Leu Glu Ala
            850                 855                 860
Arg Ile His Glu Gly Cys Glu Glu Pro Ala Thr His Asn Ala Leu Ala
865                 870                 875                 880
Lys Ile Tyr Ile Asp Ser Asn Asn Asn Pro Glu Arg Phe Leu Arg Glu
            885                 890                 895
Asn Pro Tyr Tyr Asp Ser Arg Val Val Gly Lys Tyr Cys Glu Lys Arg
            900                 905                 910
Asp Pro His Leu Ala Cys Val Ala Tyr Glu Arg Gly Gln Cys Asp Leu
            915                 920                 925
Glu Leu Ile Asn Val Cys Asn Glu Asn Ser Leu Phe Lys Ser Leu Ser
            930                 935                 940
Arg Tyr Leu Val Arg Arg Lys Asp Pro Glu Leu Trp Gly Ser Val Leu
945                 950                 955                 960
Leu Glu Ser Asn Pro Tyr Arg Arg Pro Leu Ile Asp Gln Val Val Gln
            965                 970                 975
Thr Ala Leu Ser Glu Thr Gln Asp Pro Glu Glu Val Ser Val Thr Val
            980                 985                 990
Lys Ala Phe Met Thr Ala Asp Leu Pro Asn Glu Leu Ile Glu Leu Leu
            995                 1000                1005
Glu Lys Ile Val Leu Asp Asn Ser Val Phe Ser Glu His Arg Asn Leu
            1010                1015                1020
Gln Asn Leu Leu Ile Leu Thr Ala Ile Lys Ala Asp Arg Thr Arg Val
1025                1030                1035                1040
Met Glu Tyr Ile Asn Arg Leu Asp Asn Tyr Asp Ala Pro Asp Ile Ala
            1045                1050                1055
Asn Ile Ala Ile Ser Asn Glu Leu Phe Glu Glu Ala Phe Ala Ile Phe
            1060                1065                1070
Arg Lys Phe Asp Val Asn Thr Ser Ala Val Gln Val Leu Ile Glu His
            1075                1080                1085
Ile Gly Asn Leu Asp Arg Ala Tyr Glu Phe Ala Glu Arg Cys Asn Glu
            1090                1095                1100
Pro Ala Val Trp Ser Gln Leu Ala Lys Ala Gln Leu Gln Lys Gly Met
1105                1110                1115                1120
Val Lys Glu Ala Ile Asp Ser Tyr Ile Lys Ala Asp Asp Pro Ser Ser
            1125                1130                1135
Tyr Met Glu Val Val Gln Ala Ala Asn Thr Ser Gly Asn Trp Glu Glu
            1140                1145                1150
```

-continued

Leu Val Lys Tyr Leu Gln Met Ala Arg Lys Ala Arg Glu Ser Tyr
            1155                1160                1165

Val Glu Thr Glu Leu Ile Phe Ala Leu Ala Lys Thr Asn Arg Leu Ala
    1170                1175                1180

Glu Leu Glu Glu Phe Ile Asn Gly Pro Asn Asn Ala His Ile Gln Gln
1185                1190                1195                1200

Val Gly Asp Arg Cys Tyr Asp Glu Lys Met Tyr Asp Ala Ala Lys Leu
                1205                1210                1215

Leu Tyr Asn Asn Val Ser Asn Phe Gly Arg Leu Ala Ser Thr Leu Val
            1220                1225                1230

His Leu Gly Glu Tyr Gln Ala Ala Val Asp Gly Ala Arg Lys Ala Asn
            1235                1240                1245

Ser Thr Arg Thr Trp Lys Glu Val Cys Phe Ala Cys Val Asp Gly Lys
            1250                1255                1260

Glu Phe Arg Leu Ala Gln Met Cys Gly Leu His Ile Val Val His Ala
1265                1270                1275                1280

Asp Glu Leu Glu Glu Leu Ile Asn Tyr Tyr Gln Asp Arg Gly Tyr Phe
                1285                1290                1295

Glu Glu Leu Ile Thr Met Leu Glu Ala Ala Leu Gly Leu Glu Arg Ala
            1300                1305                1310

His Met Gly Met Phe Thr Glu Leu Ala Ile Leu Tyr Ser Lys Phe Lys
            1315                1320                1325

Pro Gln Lys Met Arg Glu His Leu Glu Leu Phe Trp Ser Arg Val Asn
            1330                1335                1340

Ile Pro Lys Val Leu Arg Ala Ala Glu Gln Ala His Leu Trp Ala Glu
1345                1350                1355                1360

Leu Val Phe Leu Tyr Asp Lys Tyr Glu Glu Tyr Asp Asn Ala Ile Ile
                1365                1370                1375

Thr Met Met Asn His Pro Thr Asp Ala Trp Lys Glu Gly Gln Phe Lys
            1380                1385                1390

Asp Ile Ile Thr Lys Val Ala Asn Val Glu Leu Tyr Tyr Arg Ala Ile
            1395                1400                1405

Gln Phe Tyr Leu Glu Phe Lys Pro Leu Leu Leu Asn Asp Leu Leu Met
            1410                1415                1420

Val Leu Ser Pro Arg Leu Asp His Thr Arg Ala Val Asn Tyr Phe Ser
1425                1430                1435                1440

Lys Val Lys Gln Leu Pro Leu Val Lys Pro Tyr Leu Arg Ser Val Gln
                1445                1450                1455

Asn His Asn Asn Lys Ser Val Asn Glu Ser Leu Asn Asn Leu Phe Ile
            1460                1465                1470

Thr Glu Glu Asp Tyr Gln Ala Leu Arg Thr Ser Ile Asp Ala Tyr Asp
            1475                1480                1485

Asn Phe Asp Asn Ile Ser Leu Ala Gln Arg Leu Glu Lys His Glu Leu
            1490                1495                1500

Ile Glu Phe Arg Arg Ile Ala Ala Tyr Leu Phe Lys Gly Asn Asn Arg
1505                1510                1515                1520

Trp Lys Gln Ser Val Glu Leu Cys Lys Lys Asp Ser Leu Tyr Lys Asp
                1525                1530                1535

Ala Met Gln Tyr Ala Ser Glu Ser Lys Asp Thr Glu Leu Ala Glu Glu
            1540                1545                1550

Leu Leu Gln Trp Phe Leu Gln Glu Glu Lys Arg Glu Cys Phe Gly Ala
            1555                1560                1565

Cys Leu Phe Thr Cys Tyr Asp Leu Leu Arg Pro Asp Val Val Leu Glu

-continued

```
                1570                1575                1580
Thr Ala Trp Arg His Asn Ile Met Asp Phe Ala Met Pro Tyr Phe Ile
1585                1590                1595                1600

Gln Val Met Lys Glu Tyr Leu Thr Lys Val Asp Lys Leu Asp Ala Ser
                1605                1610                1615

Glu Ser Leu Arg Lys Glu Glu Gln Ala Thr Glu Thr Gln Pro Ile
                1620                1625                1630

Val Tyr Gly Gln Pro Gln Leu Met Leu Thr Ala Gly Pro Ser Val Ala
                1635                1640                1645

Val Pro Pro Gln Ala Pro Phe Gly Tyr Gly Tyr Thr Ala Pro Pro Tyr
                1650                1655                1660

Gly Gln Pro Gln Pro Gly Phe Gly Tyr Ser Met
1665                1670                1675

<210> SEQ ID NO 7
<211> LENGTH: 903
<212> TYPE: PRT
<213> ORGANISM: Homo sapiens

<400> SEQUENCE: 7

Met Ala Ile Gln Phe Arg Ser Leu Phe Pro Leu Ala Leu Pro Gly Met
  1               5                  10                  15

Leu Ala Leu Leu Gly Trp Trp Trp Phe Ser Arg Lys Lys Gly His
                 20                  25                  30

Val Ser Ser His Asp Glu Gln Gln Val Glu Ala Gly Ala Val Gln Leu
                 35                  40                  45

Arg Ala Asp Pro Ala Ile Lys Glu Pro Leu Pro Val Glu Asp Val Cys
         50                  55                  60

Pro Lys Val Val Ser Thr Pro Pro Ser Val Thr Glu Pro Pro Glu Lys
 65                  70                  75                  80

Glu Leu Ser Thr Val Ser Lys Leu Pro Ala Glu Pro Pro Ala Leu Leu
                 85                  90                  95

Gln Thr His Pro Pro Cys Arg Arg Ser Glu Ser Ser Gly Ile Leu Pro
                100                 105                 110

Asn Thr Thr Asp Met Arg Leu Arg Pro Gly Thr Arg Arg Asp Asp Ser
                115                 120                 125

Thr Lys Leu Glu Leu Ala Leu Thr Gly Gly Glu Ala Lys Ser Ile Pro
        130                 135                 140

Leu Glu Cys Pro Leu Ser Ser Pro Lys Gly Val Leu Phe Ser Ser Lys
145                 150                 155                 160

Ser Ala Glu Val Cys Lys Gln Asp Ser Pro Phe Ser Arg Val Pro Arg
                165                 170                 175

Lys Val Gln Pro Gly Tyr Pro Val Val Pro Ala Glu Lys Arg Ser Ser
                180                 185                 190

Gly Glu Arg Ala Arg Glu Thr Gly Gly Ala Glu Gly Thr Gly Asp Ala
        195                 200                 205

Val Leu Gly Glu Lys Val Leu Glu Glu Ala Leu Leu Ser Arg Glu His
        210                 215                 220

Val Leu Glu Leu Glu Asn Ser Lys Gly Pro Ser Leu Ala Ser Leu Glu
225                 230                 235                 240

Gly Glu Glu Asp Lys Gly Lys Ser Ser Ser Gln Val Val Gly Pro
                245                 250                 255

Val Gln Glu Glu Glu Tyr Val Ala Glu Lys Leu Pro Ser Arg Phe Ile
                260                 265                 270
```

-continued

```
Glu Ser Ala His Thr Glu Leu Ala Lys Asp Ala Ala Pro Ala Pro
    275                 280                 285
Pro Val Ala Asp Ala Lys Ala Gln Asp Arg Gly Val Glu Gly Glu Leu
290                 295                 300
Gly Asn Glu Glu Ser Leu Asp Arg Asn Glu Glu Gly Leu Asp Arg Asn
305                 310                 315                 320
Glu Glu Gly Leu Asp Arg Asn Glu Glu Ser Leu Asp Arg Asn Glu Glu
                325                 330                 335
Gly Leu Asp Arg Asn Glu Glu Ile Lys Arg Ala Ala Phe Gln Ile Ile
                340                 345                 350
Ser Gln Val Ile Ser Glu Ala Thr Glu Gln Val Leu Ala Thr Thr Val
                355                 360                 365
Gly Lys Val Ala Gly Arg Val Cys Gln Ala Ser Gln Leu Gln Gly Gln
    370                 375                 380
Lys Glu Glu Ser Cys Val Pro Val His Gln Lys Thr Val Leu Gly Pro
385                 390                 395                 400
Asp Thr Ala Glu Pro Ala Thr Ala Glu Ala Val Ala Pro Pro Asp
                405                 410                 415
Ala Gly Leu Pro Leu Pro Gly Leu Pro Ala Glu Gly Ser Pro Pro
                420                 425                 430
Lys Thr Tyr Val Ser Cys Leu Lys Ser Leu Leu Ser Pro Thr Lys
                435                 440                 445
Asp Ser Lys Pro Asn Ile Ser Ala His His Ile Ser Leu Ala Ser Cys
450                 455                 460
Leu Ala Leu Thr Thr Pro Ser Glu Glu Leu Pro Asp Arg Ala Gly Ile
465                 470                 475                 480
Leu Val Glu Asp Ala Thr Cys Val Thr Cys Met Ser Asp Ser Ser Gln
                485                 490                 495
Ser Val Pro Leu Val Ala Ser Pro Gly His Cys Ser Asp Ser Phe Ser
                500                 505                 510
Thr Ser Gly Leu Glu Asp Ser Cys Thr Glu Thr Ser Ser Pro Arg
                515                 520                 525
Asp Lys Ala Ile Thr Pro Pro Leu Pro Glu Ser Thr Val Pro Phe Ser
530                 535                 540
Asn Gly Val Leu Lys Gly Glu Leu Ser Asp Leu Gly Ala Glu Asp Gly
545                 550                 555                 560
Trp Thr Met Asp Ala Glu Ala Asp His Ser Gly Gly Ser Asp Arg Asn
                565                 570                 575
Ser Met Asp Ser Val Asp Ser Cys Cys Ser Leu Lys Lys Thr Glu Ser
                580                 585                 590
Phe Gln Asn Ala Gln Ala Gly Ser Asn Pro Lys Lys Val Asp Leu Ile
    595                 600                 605
Ile Trp Glu Ile Glu Val Pro Lys His Leu Val Gly Arg Leu Ile Gly
    610                 615                 620
Lys Gln Gly Arg Tyr Val Ser Phe Leu Lys Gln Thr Ser Gly Ala Lys
625                 630                 635                 640
Ile Tyr Ile Ser Thr Leu Pro Tyr Thr Gln Ser Val Gln Ile Cys His
                645                 650                 655
Ile Glu Gly Ser Gln His His Val Asp Lys Ala Leu Asn Leu Ile Gly
                660                 665                 670
Lys Lys Phe Lys Glu Leu Asn Leu Thr Asn Ile Tyr Ala Pro Pro Leu
    675                 680                 685
Pro Ser Leu Ala Leu Pro Ser Leu Pro Met Thr Ser Trp Leu Met Leu
```

-continued

```
            690                 695                 700
Pro Asp Gly Ile Thr Val Glu Val Ile Val Asn Gln Val Asn Ala
705                 710                 715                 720

Gly His Leu Phe Val Gln Gln His Thr His Pro Thr Phe His Ala Leu
                    725                 730                 735

Arg Ser Leu Asp Gln Gln Met Tyr Leu Cys Tyr Ser Gln Pro Gly Ile
                740                 745                 750

Pro Thr Leu Pro Thr Pro Val Glu Ile Thr Val Ile Cys Ala Ala Pro
                755                 760                 765

Gly Ala Asp Gly Ala Trp Trp Arg Ala Gln Val Val Ala Ser Tyr Glu
770                 775                 780

Glu Thr Asn Glu Val Glu Ile Arg Tyr Val Asp Tyr Gly Gly Tyr Lys
785                 790                 795                 800

Arg Val Lys Val Asp Val Leu Arg Gln Ile Arg Ser Asp Phe Val Thr
                805                 810                 815

Leu Pro Phe Gln Gly Ala Glu Val Leu Leu Asp Ser Val Met Pro Leu
                820                 825                 830

Ser Asp Asp Gln Phe Ser Pro Glu Ala Asp Ala Ala Met Ser Glu
835                 840                 845

Met Thr Gly Asn Thr Ala Leu Leu Ala Gln Val Thr Ser Tyr Ser Pro
850                 855                 860

Thr Gly Leu Pro Leu Ile Gln Leu Trp Ser Val Val Gly Asp Glu Val
865                 870                 875                 880

Val Leu Ile Asn Arg Ser Leu Val Glu Arg Gly Leu Ala Gln Trp Val
                885                 890                 895

Asp Ser Tyr Tyr Thr Ser Leu
                900

<210> SEQ ID NO 8
<211> LENGTH: 197
<212> TYPE: PRT
<213> ORGANISM: Homo sapiens

<400> SEQUENCE: 8

Met Met Phe Pro Gln Ser Arg His Ser Gly Ser Ser His Leu Pro Gln
1               5                   10                  15

Gln Leu Lys Phe Thr Thr Ser Asp Ser Cys Asp Arg Ile Thr Asp Glu
                20                  25                  30

Phe Gln Leu Leu Gln Ala Gln Tyr His Ser Leu Lys Leu Glu Cys Asp
            35                  40                  45

Lys Leu Ala Ser Glu Lys Ser Glu Met Gln Arg His Tyr Val Met Tyr
50                  55                  60

Tyr Glu Met Ser Tyr Gly Leu Asn Ile Glu Met His Lys Gln Ala Glu
65                  70                  75                  80

Ile Val Lys Arg Leu Asn Gly Ile Cys Ala Gln Val Leu Pro Tyr Leu
                85                  90                  95

Ser Gln Glu His Gln Gln Gln Val Leu Gly Ala Ile Glu Arg Ala Lys
            100                 105                 110

Gln Val Thr Ala Pro Glu Leu Asn Ser Ile Ile Arg Gln Gln Leu Gln
        115                 120                 125

Ala His Gln Leu Ser Gln Leu Gln Ala Leu Ala Leu Pro Leu Thr Pro
    130                 135                 140

Leu Pro Val Gly Leu Gln Pro Pro Ser Leu Pro Ala Val Ser Ala Gly
145                 150                 155                 160
```

```
Thr Gly Leu Leu Ser Leu Ser Ala Leu Gly Ser Gln Ala His Leu Ser
                165                 170                 175

Lys Glu Asp Lys Asn Gly His Asp Gly Asp Thr His Gln Glu Asp Asp
            180                 185                 190

Gly Glu Lys Ser Asp
        195

<210> SEQ ID NO 9
<211> LENGTH: 33
<212> TYPE: DNA
<213> ORGANISM: Artificial Sequence
<220> FEATURE:
<223> OTHER INFORMATION: PCR primer

<400> SEQUENCE: 9
cgcggatccc catgcaggcg cgctactccg tgt                         33

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
cgcggatcct cagtatttcg tgcagtcgta gga                         33

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
taatacgact cactataggg                                        20

<210> SEQ ID NO 12
<211> LENGTH: 19
<212> TYPE: DNA
<213> ORGANISM: Artificial Sequence
<220> FEATURE:
<223> OTHER INFORMATION: PCR primer

<400> SEQUENCE: 12
agggcgtgaa tgtaagcgt                                         19
```